June 7, 1960 F. W. ANDERSON Plant Pat. 1,949

NECTARINE TREE

Filed Aug. 17, 1959

WITNESS

Addison E. Avery

INVENTOR

Frederic W. Anderson

Webster & Webster

ATTYS.

United States Patent Office

Plant Pat. 1,949
Patented June 7, 1960

1,949

NECTARINE TREE

Frederic W. Anderson, Merced, Calif., assignor to Stark Bro's Nurseries and Orchards Co., Louisiana, Mo., a corporation of Missouri Filed Aug. 17, 1959, Ser. No. 834,365

1 Claim. (Cl. 47—62)

This invention relates to a new and distinct variety of nectarine tree which bears yellow fleshed, freestone to semi-freestone fruit having yellow skin overspread to a substantial extent with red. The variety is of the type embraced by group 113 of the classification by Caillavet and Souty, Monographie des Principales Variétés de Pêchers, 1950 edition, page 46.

As compared with the John Rivers nectarine (unpatented) the fruit of the present variety ripens a few days earlier and is of superior commercial quality in that it is larger, firmer, has yellow instead of white flesh, and is more attractive by reason of a greater amount of red exterior color.

As compared with the Grand River nectarine (United States Plant Patent No. 1,248) the ripening period is approximately the same, but the fruit is firmer at the apical end, has more red exterior color, and arrives at market—and after long distance shipment—in a better and more attractive condition.

The fruit of the present variety of nectarine tree is genetically a freestone and is free when tree-ripened, but clings somewhat under cool growing conditions and when picked before full ripe.

The instant variety of nectarine tree was originated by me in my experimental orchard located near Merced, California, and is a cross between the Sun Grand nectarine (United States Plant Patent No. 974) and a commercially unnamed peach (unpatented); such unnamed peach having been previously originated by me as a cross between the Le Grand nectarine (United States Plant Patent No. 549) and the Merrill Gem peach (United States Plant Patent No. 868).

Subsequent to its origination, as above, it was observed that the variety was advantageously characterized, as hereinbefore described, and I therefore selected it for reproduction. The variety was asexually reproduced by me by topworking on mature orchard trees in my experimental orchard located as aforesaid; such reproductions having been found to run true in all respects.

Figures 1, 2:
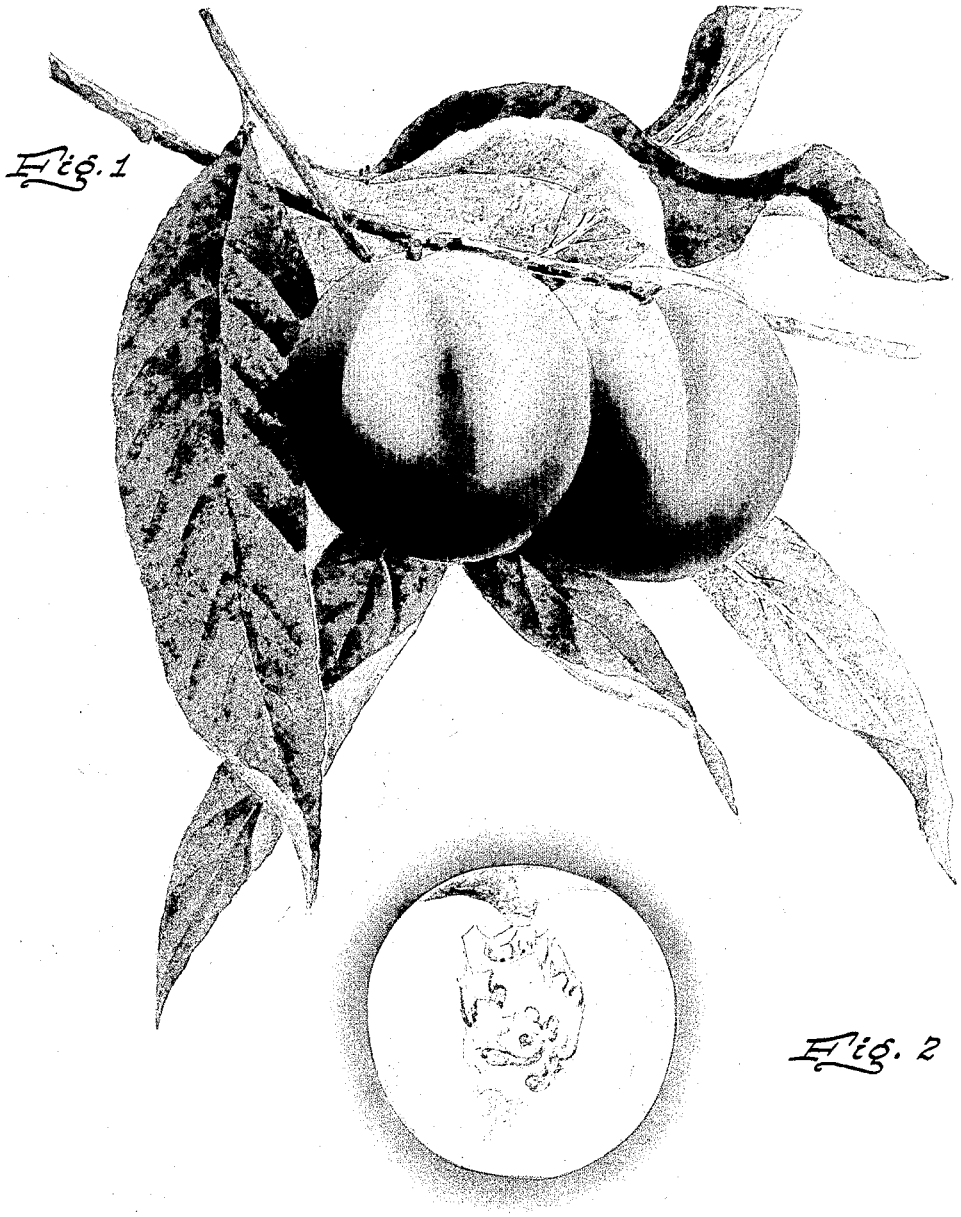
Fig. 1 is an elevation showing two of the nectarines, together with twigs and leaves.
Fig. 2 is a sectional elevation of one of the nectarines with the stone remaining in place.

Referring to pomological details of this new and distinct variety of nectarine tree and its fruit, the following is an outline description thereof; all major color plate identifications being by reference to Maerz and Paul Dictionary of Color.

Tree:
- *Size.*—Medium.
- *Vigor.*—Vigorous.
- *Form.*—Upright to spreading.
- *Production.*—Productive.
- *Bearing.*—Regular bearer.

Trunk:
- *Size.*—Medium.
- *Texture.*—Medium.

Branches:
- *Size.*—Medium.
- *Texture.*—Medium.

Leaves:
- *Size.* — Medium. Average length — 6". Average width—1½".
- *Form.*—Oval; acutely pointed.
- *Thickness.*—Medium.
- *Texture.*—Smooth.
- *Margin.*—Crenate.
- *Petiole.*—Medium length.
- *Glands.* — Opposite; medium size; globose. Position—usually two on petiole, and two or more on blade. Stipules fall very early.
- *Color.*—Top side—medium green (22–L–7). Under side—slightly lighter green (22–K–6).

Flower buds:
- *Size.*—Medium.
- *Length.*—Medium.
- *Pubescence.*—Pubescent.

Flowers:
- *Blooming period.*—Medium compared with other varieties.
- *Size.*—Large.
- *Type.*—Showy.

Fruit:
- *Maturity when described.*—Eating ripe—June 24, 1958.
- *Date of first picking.*—June 17, 1958.
- *Date of last picking.*—June 27, 1958.
- *Size.*—Large to medium. Average diameter axially—2½". Average transversely in suture plane—2½".
- *Form.*—Uniform; symmetrical; globose.
- *Suture.*—Shallow, with slight depression beyond pistil point.
- *Ventral surface.*—Rounded slightly.
- *Cavity.*—Rounded.
- *Base.*—Rounded.
- *Apex.*—Short.

Skin:
- *Thickness.*—Medium.
- *Texture.*—Medium.
- *Tendency to crack.*—None.
- *Down.*—Wanting.
- *Color.*—Yellow (9–L–6 to 10–L–8), overspread to a substantial extent with red (3–L–11) shading to darker red (6–L–6).

Flesh:
- *Texture.*—Firm to medium; meaty.
- *Ripens.*—Even.
- *Flavor.*—Subacid.
- *Aroma.*—Distinct.
- *Eating quality.*—Fair to good.
- *Color.*—Yellow (10–K–5) near the stone, shading outwardly somewhat darker (10–K–8), with a reddish cast or slight mottling (3–J–10) near the skin.

Stone:
- *Type.*—Free to semi-free.
- *Size.*—Medium.
- *Tendency to split.*—Slight.
- *Color.*—Tan (3–A–10).

Use: Market; local; long distance shipping.
Keeping quality: Good to medium.
Shipping quality: Good.

The tree and its fruit herein described may vary in slight detail due to climatic and soil conditions under which the variety may be grown; the present description being of the variety as grown in the Central Valley of California.

The following is claimed:

A new and distinct variety of nectarine tree, as illustrated and described, which bears yellow fleshed freestone to semi-freestone fruit having skin which is yellow overspread to a substantial extent with red; characterized—in comparison with the John Rivers nectarine—by fruit which ripens a few days earlier, is larger and firmer, has yellow instead of white flesh, and has more red exterior color; and further characterized by fruit which ripens approximately with the Grand River nectarine but—in comparison—is firmer at the apical end, has more red exterior color, and better withstands long distance shipment.

No references cited.